(12) United States Patent
Sancilio et al.

(10) Patent No.: US 12,344,583 B2
(45) Date of Patent: *Jul. 1, 2025

(54) SOLID PSILOCIN SALTS

(71) Applicant: LOBE SCIENCES LTD., Vancouver (CA)

(72) Inventors: Frederick Sancilio, Stuart, FL (US);
Yousry Sayed, Wilmington, NC (US);
Maghsoud Dariani, Fanwood, NJ (US);
Scott Mough, Wilmington, NC (US);
Shaileshkumar Ramanlal Desai, Wilmington, NC (US); Autumn Beauchamp, Wilmington, NC (US)

(73) Assignee: Lobe Sciences Ltd., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/888,371

(22) Filed: Sep. 18, 2024

(65) Prior Publication Data

US 2025/0019348 A1 Jan. 16, 2025

Related U.S. Application Data

(63) Continuation-in-part of application No. PCT/US2023/027500, filed on Jul. 12, 2023.

(60) Provisional application No. 63/573,567, filed on Apr. 3, 2024, provisional application No. 63/388,414, filed on Jul. 12, 2022.

(51) Int. Cl.
| | |
|---|---|
| *C07D 209/16* | (2006.01) |
| *A61K 9/00* | (2006.01) |
| *A61K 9/48* | (2006.01) |
| *A61K 31/4045* | (2006.01) |
| *A61K 31/675* | (2006.01) |

(52) U.S. Cl.
CPC .......... *C07D 209/16* (2013.01); *A61K 9/0053* (2013.01); *A61K 9/4825* (2013.01); *A61K 31/4045* (2013.01); *A61K 31/675* (2013.01)

(58) Field of Classification Search
CPC ........................ C07D 209/16; A61K 31/4045; A61K 31/454; A61K 31/675; A61K 9/0053; A61K 9/4825; A61P 25/00
See application file for complete search history.

(56) References Cited

U.S. PATENT DOCUMENTS

| | | | |
|---|---|---|---|
| 3,078,214 A | 2/1963 | Hoffman et al. | 167/65 |
| 11,312,684 B1 | 4/2022 | Nichols et al. | C07D 209/16 |
| 12,102,616 B2 * | 10/2024 | Sayed | C07D 209/16 |
| 12,178,801 B1 * | 12/2024 | Sayed | A61K 47/542 |
| 2004/0242801 A1 | 12/2004 | Petit et al. | 525/353 |
| 2018/0021326 A1 | 1/2018 | Stamets | A61K 31/455 |
| 2022/0280482 A1 | 9/2022 | Barrow et al. | A61K 31/4045 |
| 2022/0370413 A1 | 11/2022 | Barrow et al. | A61K 31/4045 |
| 2023/0285359 A1 | 9/2023 | Barrow et al. | A61K 31/4045 |

FOREIGN PATENT DOCUMENTS

| | | |
|---|---|---|
| WO | 2020/157569 | 8/2020 |
| WO | 2022/016289 | 1/2022 |
| WO | 2022/195489 | 9/2022 |
| WO | 2023/086962 | 5/2023 |

OTHER PUBLICATIONS

U.S. Appl. No. 18/992,641, filed Jan. 9, 2025, Sayed; Yousry.*
Brown et al. "Pharmacokinetics of Escalating Doses of Oral Psilocybin in Healthy Adults" Clin Pharmacokinet 2017 56:1543-1554.
Griffith et al. "Psilocybin occasioned mystical-type experiences: immediate and persisting dose-related effects" Pschopharmacology 2011 218:649-665.
Hasler et al. "Determination of psilocin and 4-hydroxyindole-3-acetic acid in plasma by HPLC-ECD and pharmacokinetic profiles of oral and intravenous psilocybin in man" Pharmaceutica Acta Helvetiae 1997 72(3), 175-184.
Holze et al. "Pharmacokinetics and Pharmacodynamics of Oral Psilocybin Administration in Healthy Participants" Clinical Pharmacology & Therapeutics 2023 113(4):822-831.
International Search Report and Written Opinion in PCT/US2023/027500 dated Oct. 13, 2023.
Kolaczynska et al. "Development and validation of an LC-MS/MS method for the bioanalysis of psilocybin's main metabolites, psilocin and 4-hydroxyindole-3-acetic acid, in human plasma" Journal of Chromatography 2021 B1164 122486 pp. 1-10.
Lindenblatt et al. "Quantitation of psilocin in human plasma by high-performance liquid chromatography and electrochemical detection: comparison of liquid-liquid extraction with automated on-line solid-phase extraction" Journal of Chromatography 1998 709:255-263.
Psilocybin Investigator Brochure by Usona Institute Jun. 17, 2021 72 pages.
Troxler et al. "Abwandlungsprodukte von Psilocybin and Psilocin" Helvetica Chimica Acta 1959 42(6):2073-2103.
Tylš et al. "Psilocybin—Summary of knowledge and new perspectives" European Neuropsychopharmacology 2014 24(3): 342-356).
Office Communication dated Mar. 15, 2024 in U.S. Appl. No. 18/411,576, filed Jan. 12, 2024.
Office Communication dated May 22, 2024 in U.S. Appl. No. 18/411,576, filed Jan. 12, 2024.
U.S. Appl. No. 18/818,317, filed Aug. 28, 2024.

* cited by examiner

*Primary Examiner* — Kara R. McMillian
(74) *Attorney, Agent, or Firm* — Licata & Tyrrell P.C.

(57) ABSTRACT

Solid forms of psilocin and methods for their production and use with one or more improved properties as compared to psilocin and amorphous psilocin salts thereof are provided.

12 Claims, 2 Drawing Sheets

SOLID PSILOCIN SALTS

This patent application claims the benefit of priority from U.S. Provisional Application Ser. No. 63/573,567 filed Apr. 3, 2024 and is a continuation-in-part of PCT/US2023/027500 filed Jul. 12, 2023, which claims the benefit of priority from U.S. Provisional Application Ser. No. 63/388,414 filed Jul. 12, 2022, teachings of each of which are incorporated herein by reference in their entirety.

FIELD

This disclosure relates to solid psilocin salts and methods for production of solid psilocin salts, at least a portion of which is crystalline and which exhibit one or more improved properties as compared to psilocin and amorphous psilocin salts.

BACKGROUND

Psilocybin, structure of which is depicted in Formula I

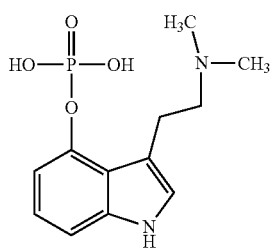

is a phosphate ester prodrug for psilocin as depicted in Formula II

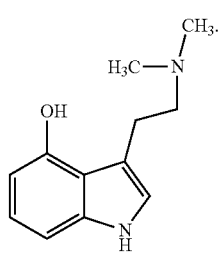

When administered to a subject, psilocybin is metabolized to form psilocin. Psilocybin undergoes an acid catalyzed and/or enzymatic dephosphorylation reaction resulting in a loss of the phosphate group revealing psilocin's hydroxy group. Psilocybin exists as a zwitterion in which the phosphate and amine moiety ionize each other. The existence of a zwitterion limits the solubility of psilocybin and also curtails its ability to make a salt with an alternate acid that could exist under physiologically tolerated conditions. Removing the phosphate group allows the formation of an intermolecular salt of psilocin that is otherwise not possible to be prepared with psilocybin. As a non-ionized form, psilocin is much more lipid soluble in comparison to psilocybin, and therefore is capable of crossing the blood brain barrier more effectively to elicit a response. Psilocin has a high affinity for and is able to activate the 5-HT2A receptor, which plays a key role in regulating mood, sexual behavior, aggression, impulsivity, cognitive function, appetite, pain, sleep, and memory along with other behaviors.

Evidence of therapeutic effects of psilocin in a wide array of clinical applications, including psychiatric conditions, pain disorders, and neurological conditions, has resulted in significant interest in this compound. However, poor physical properties of psilocin in the solid state, e.g. poor crystallinity with limited enhancement of bulk purity upon crystallization, susceptibility to auto-catalyzed oxidation upon handling and prolonged storage, and low water solubility have hampered development of psilocin-based pharmaceuticals.

Classic psychedelics, which are serotonergic hallucinogens, like psilocin, have been shown in multiple lines of research to potentially induce therapeutic changes in people with a variety of psychiatric conditions. However, as natural psilocin is only found in relatively smaller amounts in the actual mushroom (Tylš et al. European Neuropsychopharmacology 2014 24 (3): 342-356) and unmodified psilocin is relatively unstable in solution, most research has focused on the prodrug, psilocybin, which is metabolized to psilocin after ingestion and responsible for the shown therapeutic and behavioral effects.

Results of completed and published studies have shown psilocin exposure (through psilocybin administration) to results in significant improvement in symptoms of anxiety, depression, and substance use disorder.

Further, psilocin's clinical safety have been extensively studied, both as a single agent and as an adjunctive treatment in adult populations. Psilocin was most commonly administered as psilocybin capsules through oral administration and has been assessed in open-label and double-blind, controlled trials. Dosing regimens for psilocybin have ranged from 0.014 mg/kg to 0.6 mg/kg (which roughly correspond to dose ranges of 7 µg/kg-0.32 mg/kg of psilocin based on estimated dose-normalized bioavailability of 52.7% from (F. Hasler et al. Pharmaceutica Acta Helvetiae 1997 72 (3), 175-184), administered either as a single dose, or multiple escalating doses weeks apart.

Among adverse psychological experiences, the ones often reported include anxiety, the induction of negative emotional states, and paranoid or delusional thinking. In relation to physical adverse events, they are cardiovascular (i.e., increased blood pressure and heart rate), as well as nausea and headache. Further, reports of a hallucinogenic effects coupled with increased anxiety have been reports at does as low as 5 mg psilocybin which is equivalent to about 2 mg psilocin. See, e.g. Griffith et al. Pharmaceutica Acta Helvetiae 2011 72 (3) 175-184.

U.S. Pat. No. 11,312,684 discloses psilocin benzoate and psilocin succinate salts to be preferred salt forms for producing a pharmaceutical composition with superior shelf-life stability, and resistance to oxidative degradation. Stability for up to three weeks is disclosed for some of their salts.

There exists a need for solid forms of psilocin salts with improved stability, physical properties and/or handling characteristics as compared to psilocin.

SUMMARY

An aspect of this disclosure relates to solid forms of psilocin salts.

In one nonlimiting embodiment, at least a portion of the solid psilocin salt is in crystalline form.

In one nonlimiting embodiment, the crystalline portion of the solid psilocin salt is characterized by an X-ray powder diffraction (XRPD) pattern comprising peaks at about 14.71, 15.75, 19.57 and 23.20 2θ,° using Cu Kα radiation.

In one nonlimiting embodiment, the solid psilocin salt is psilocin mucate.

Another aspect of this disclosure relates to pharmaceutical compositions comprising a solid form of psilocin salt and a pharmaceutically acceptable carrier.

In one nonlimiting embodiment, at least a portion of the solid form of psilocin salt in the pharmaceutical composition is in crystalline form.

In one nonlimiting embodiment, the crystalline portion of the solid psilocin salt is characterized by an X-ray powder diffraction (XRPD) pattern comprising peaks at about 14.71, 15.75, 19.57 and 23.20 2θ,° using Cu Kα radiation.

In one nonlimiting embodiment, the solid psilocin salt in the pharmaceutical composition is psilocin mucate.

Yet another aspect of this disclosure relates to methods for use of the solid forms of psilocin and pharmaceutical compositions thereof in treating conditions and diseases treatable with psilocin or psilocybin.

In one nonlimiting embodiment, at least a portion of the solid form of psilocin salt used in these methods is in crystalline form.

In one nonlimiting embodiment, the crystalline portion of the solid psilocin salt is characterized by an X-ray powder diffraction (XRPD) pattern comprising peaks at about 14.71, 15.75, 19.57 and 23.20 2θ,° using Cu Kα radiation.

In one nonlimiting embodiment, the solid form of psilocin used in these methods is psilocin mucate.

DEFINITIONS

Figure 1:
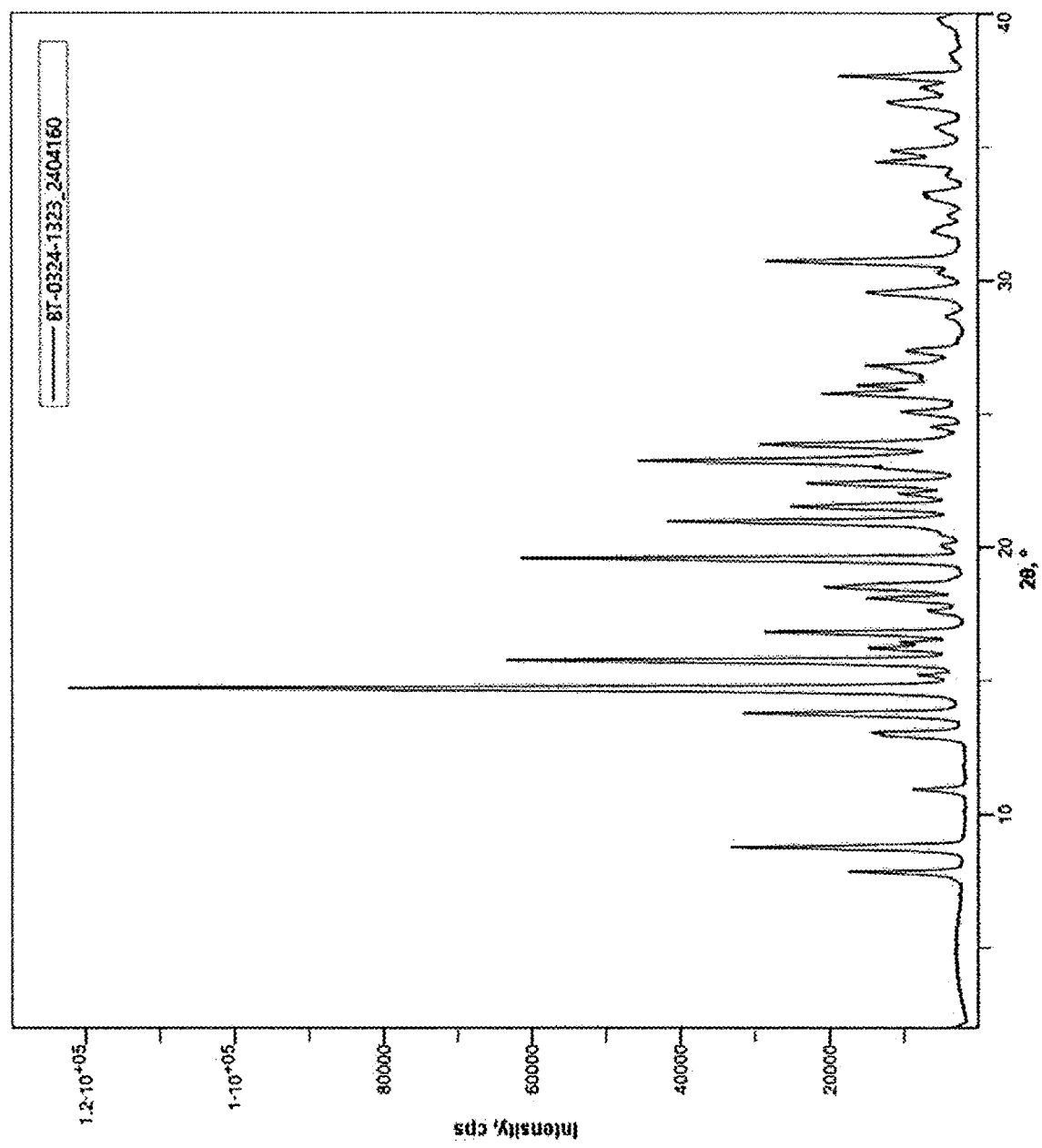
FIG. 1 is an X-ray diffraction pattern for a solid psilocin mucate salt of this disclosure in crystalline form. A corresponding list of measured peaks is set forth herein in Table 2.

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

Terms such as "a", "an," and "the" are not intended to refer to only a singular entity but include the general class of which a specific example may be used for illustration.

As used herein, the term "about" refers to a value that is within 10% above or below the value being described.

The term "administration" or "administering" refers to a method of giving a dosage of a compound or pharmaceutical composition to a subject.

As used herein, the phrases "pharmacologically effective amount," "therapeutically effective amount," and the like, when used in reference to psilocin salts, esters and conjugates and pharmaceutical compositions comprising these salts, esters and conjugates as disclosed herein, refer to a quantity sufficient to, when administered to the subject, including a mammal, such as a human, which alleviates one or more symptoms of the disease or condition for which the salt, ester or conjugates or composition thereof is administered. The quantity of a given composition described herein that will correspond to such an amount may vary depending upon various factors, such as the given agent, the pharmaceutical formulation, the route of administration, the type of disease or disorder, the identity of the subject (e.g., age, sex, weight) or host being treated, and the like.

As used herein, the terms "treat," "treating," or "treatment" refer to administration of a compound or pharmaceutical composition for a therapeutic purpose. To "treat a disorder" or use for "therapeutic treatment" refers to administering treatment to a subject already suffering from a disease to ameliorate the disease or one or more symptoms thereof to improve the subject's condition (e.g., by reducing one or more symptoms of inflammation). Compositions of the disclosure can also be used as a primary prevention measure, i.e., to prevent a condition or to reduce the risk of developing a condition. Prevention refers to prophylactic treatment of a subject who may not have fully developed a condition or disorder, but who is susceptible to, or otherwise at risk of, the condition. Thus, in the claims and embodiments, the compositions and methods of the disclosure can be used either for therapeutic or prophylactic purposes.

As used herein, the terms "salt", "salts", "salt forms", "conjugate", "conjugates" and "conjugate forms" are interchangeable and are meant to be inclusive of any compounds formed when mixing psilocin with galactaric acid (mucic acid). Without being bound to any particular theory, it is believed that salt, ester and conjugate forms of the compounds disclosed herein exhibit binding characteristics in addition to or alternatively from ionic binding of traditional salts which enhances their stability.

Other features and advantages of the disclosure will be apparent from the following Detailed Description, Examples, and Claims.

DETAILED DESCRIPTION

Disclosed herein are solid forms of psilocin salts. At least a portion of the solid form of a psilocin salt as disclosed herein is crystalline and/or polymorphic. Further, solid forms of psilocin salts of this disclosure exhibit at least one improved property compared to an amorphous psilocin salt such as, but not limited to, amorphous psilocin mucate salts.

In one nonlimiting embodiment, the solid form of psilocin salt is a solvate, such as a hydrate.

In one nonlimiting embodiment, the crystalline portion of the solid psilocin salt is characterized by an X-ray powder diffraction (XRPD) pattern comprising peaks at about 14.71, 15.75, 19:57 and 23.20 2θ,° using Cu Kα radiation. In this nonlimiting embodiment, the crystalline portion may optionally be further characterized by XRPD pattern peaks at 8.75, 20.93, 23.80 and 30.66 2θ, ° using Cu Kα radiation.

In one nonlimiting embodiment, the crystalline portion of the solid psilocin salt has a measured XRPD patterns using Cu Kα radiation as substantially shown in FIG. 1 and/or a peak list as depicted in Table 2.

Figure 2:
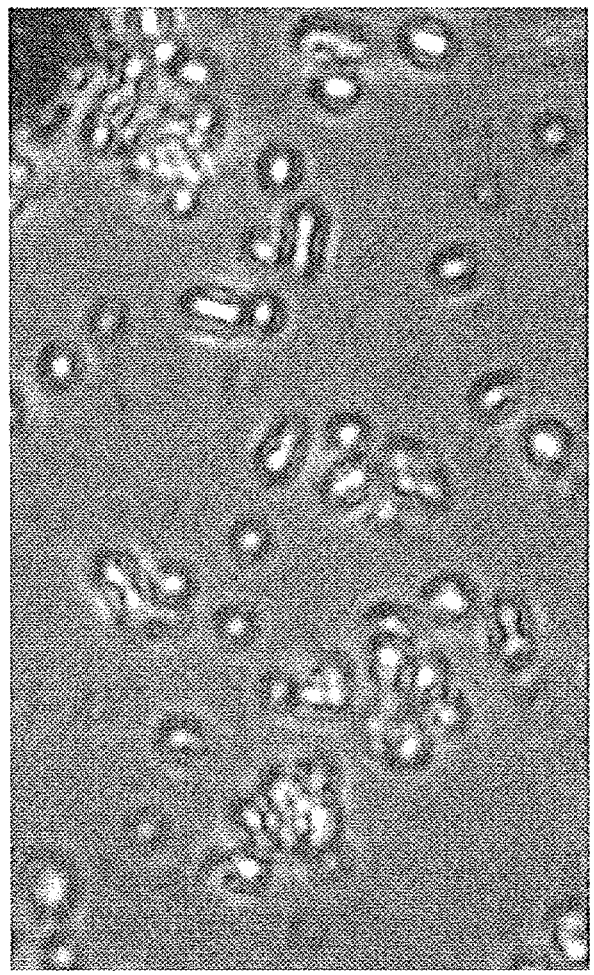
FIG. 2 is a digital image from microscopic analysis of a solid psilocin mucate salt of this disclosure in a crystalline state.

FIG. 2 provides a digital image from microscopic analysis of a psilocin mucate salt of this disclosure in a crystalline state.

In contrast, the amorphous form of psilocin mucate salt does not exhibit an X-ray diffraction pattern.

Also disclosed herein is a solid form of a psilocin mucate salt that is produced in accordance with the method described in Example 1. The solid form of psilocin mucate salt made by the disclosed method exhibits at least one improved property compared to amorphous psilocin salts including, but not limited to, amorphous psilocin mucate salts. As will be understood by the skilled artisan upon reading this disclosure, alternative methods for production of solid psilocin mucate salts in accordance with this disclosure may be used.

By "at least a portion" of the solid form of a psilocin salt being crystalline and/or polymorphic in accordance with this disclosure it is meant to include at least 35%, 40%, 45%, and 50% or greater of the solid form of psilocin salt being crystalline and/or polymorphic.

By "at least one improved property" in accordance with this disclosure, it is meant to include, but is not limited to, an improved physical property, chemical property, pharmacokinetic property, or a combination thereof. In some non-limiting embodiments, the "at least one improved property" is melting point, glass transition temperature, flowability, thermal stability, shelf life, stability against polymorphic transition, hygroscopic properties, solubility in water and/or organic solvents, reactivity, compatibility with excipients and/or delivery vehicles, bio-availability, absorption, distribution, metabolism, excretion, toxicity including cytotoxicity, dissolution rate, half-life, or a combination thereof, that is improved compared to an amorphous sample of psilocin salt including, but not limited to, amorphous psilocin mucate salts.

Psilocin solid forms of this disclosure exhibit improved stability, physical properties, and/or handling characteristics as compared to psilocin. For example, psilocin mucate was demonstrated to be stable for at least 7 months.

Further, studies in human subjects have shown that a psilocin solid form of this disclosure to exhibit a strong calming effect in patients without the hallucinogenic effect and/or anxiogenic effect often seen with psilocin administration at similar doses. Surprisingly, unlike results reported for psilocybin administration such as by Griffith et al. (Pharmaceutica Acta Helvetiae 2011 72 (3) 175-184.), 9 of 10 subjects administered a psilocin mucate at an equivalent effective dose of 2 mg psilocin had no hallucinogenic effect but a strong suggestion of an anti-anxiolytic effect. These anti-anxiolytic effects at such a low dose, without the hallucinogenic effect was completely unexpected, particularly in a patient population undergoing blood draws often during this same time period.

Also disclosed herein are pharmaceutical compositions comprising a solid psilocin form of this disclosure and a pharmaceutically acceptable carrier or excipient. The pharmaceutical compositions of this disclosure exhibit improved stability, physical properties, and/or handling characteristics as compared to psilocin containing pharmaceutical compositions. Further, studies in patients have shown that psilocin solid forms of this disclosure exhibit a strong calming effect in patients without a hallucinogenic effect and/or anxiogenic effect often seen with psilocin administration.

In general, dosing regimens found to be useful for psilocybin can also be used for the solid psilocin forms of this disclosure. In addition, microdosing via regular ingestion of a solid psilocin form as disclosed herein, at very low doses (ranging from 0.5-5 mg, depending on the condition to be treated), may also be a valid dosing approach with therapeutic potential.

Examples of a pharmaceutically acceptable excipients or carriers include, but are not limited to, biocompatible vehicles, adjuvants, additives, and diluents to achieve a composition usable as a dosage form. Examples of other excipients include colloidal silicon oxide, magnesium stearate, cellulose, sodium lauryl sulfate, and D&C Yellow #10.

Pharmaceutical compositions of this disclosure may comprise one or more solvents, diluents, or other liquid vehicles, dispersions or suspension aids, surface active agents, isotonic agents, thickening or emulsifying agents, preservatives, solid binders, and lubricants, as suited to the particular dosage form desired. Remington's Pharmaceutical Sciences, Eighteenth Edition, E. W. Martin (Mack Publishing Co., Easton, Pa., 1990) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this disclosure. Some examples of materials which can serve as pharmaceutically acceptable excipients include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine; and hydroxypropyl-beta-cyclodextrin and sulfonic acid substituted cyclodextrin (e.g., CAPTISOL™). Commercial grades of lecithin which are preferred include those which are available under the trade name Phosal® or Phospholipon®. and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; 5% dextrose solution and combinations with the foregoing aqueous solutions; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this disclosure can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

When used in the methods and compositions of the disclosure, the pharmaceutically acceptable solid psilocin forms may be contained in any appropriate amount in any suitable carrier substance formulated for intravenous infusion and is generally present in an amount of 0.01-95% by weight of the total weight of the composition. In particular embodiments, the pharmaceutically acceptable solid psilocin form is present in an amount of 0.01-5% by weight of the total weight of the composition. In some embodiments, an aqueous solution suitable for intravenous infusion including the pharmaceutically acceptable solid psilocin form may be formulated in a saline solution. The formulation of infusions is well known to those skilled in the art of pharmaceutical formulation. Formulations can be found in Remington: The Science and Practice of Pharmacy (23rd ed), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). Compositions for infusion use may be provided in unit dosage forms (e.g., in single-dose ampoules), or in vials containing several doses and in which a suitable preservative may be added. The solution of the pharmaceutically acceptable solid psilocin form suitable for intravenous infusion may have a pH of about 3 and about 9. Furthermore, the solution of the pharmaceutically acceptable solid psilocin form suitable for intravenous infusion may include a concentration of the pharmaceutically acceptable solid psilocin form between about 0.1 mg/mL and about 50 mg/mL. In some embodiments, the aqueous solution has between about 1 mg/mL and about 15 mg/mL of a solid psilocin form as described herein. In particular embodiments, the aqueous solution has between about 0.1 mg/mL and about 1 mg/mL of a solid psilocin form described herein.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acids, such as, but not limited to, oleic acid and its glyceride derivatives, are useful in the preparation of injectables, as are natural pharmaceutically acceptable oils, such as, but not limited to, olive oil or castor oil, or polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used excipients include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Preferred is that oral formulations such as capsules be packaged in amber glass bottles, secured with polypropylene caps with foam seal liner and maintained until administration at 15-25° C. in a tightly closed container in a dry location.

In one nonlimiting embodiment, the solid psilocin form is administered in a nasal spray formulation.

In one nonlimiting embodiment, the solid psilocin form is administered by nasal spray transducer programmed time release administration. A nonlimiting device for such administration is described in PCT/US2021/028068 filed Apr. 20, 2021, teachings of which are incorporated herein by reference in their entirety.

In one nonlimiting embodiment, the solid psilocin form is administered in a nasal spray where a therapeutically active amount of the solid psilocin form is dissolved or suspended in solution or mixtures of excipients (e.g., preservatives, viscosity modifiers, emulsifiers, buffering agents) in non-pressurized dispensers that deliver a spray containing a metered dose of active ingredient.

Solid psilocin forms of this disclosure and pharmaceutical compositions thereof are useful in methods of treating or alleviating symptoms of any disease or condition treatable with psilocin or psilocybin. Such methods comprise administering a solid psilocin form of this disclosure to a subject in need in an amount sufficient to treat or alleviate symptoms of the disease or condition. Nonlimiting examples of diseases or conditions include neurological injuries, neurodegenerative diseases, neurological disorders, neurodevelopmental disorders, inflammatory conditions, chronic pain, or psychological conditions. In certain embodiments, the disease or condition is an inflammatory condition (e.g., lung inflammation, neuroinflammation, rheumatoid arthritis, atherosclerosis, psoriasis, type II diabetes, inflammatory bowel disease, Crohn's disease, multiple sclerosis, and/or septicemia). In particular embodiments, the inflammatory condition is chronic obstructive pulmonary disease (COPD), or Alzheimer's disease. In certain embodiments, the disease or condition is a neurological injury (e.g., a stroke, a traumatic brain injury, or a spinal cord injury). In some embodiments, the disease or condition is chronic pain (e.g., pain resulting from post-operative pain, tension headaches, migraines, post-traumatic headaches, trigeminal neuralgia, chronic lower back pain, fibromyalgia, phantom limb pain, nephropathy, multiple sclerosis, shingles, complex regional pain syndrome, cephalic pain, or sciatica). In particular embodiments, the chronic pain condition results from trigeminal autonomic cephalalgia (e.g., episodic and chronic cluster headache (CH), episodic and chronic paroxysmal hemicrania (PH), short-lasting unilateral neuralgiform headache attacks with conjunctival injection and tearing (SUNCT) or short-lasting unilateral neuralgiform headache with cranial autonomic symptoms (SUNA)). In some embodiments, the trigeminal autonomic cephalalgia is episodic or chronic CH. In certain embodiments, the condition is a psychological condition (e.g., depression, anxiety, addiction, post-traumatic stress disorder, an eating disorder, selective mutism or compulsive behavior). In particular embodiments, the psychological condition is depression such as, but not limited to, major depressive disorder (MDD), treatment-resistant depression (TRD), bipolar depression (Bipolar Disorder Type II), depressive episodes in anxiety disorders, atypical depression, seasonal affective disorder (SAD), postpartum depression, persistent depressive disorder (dysthymia), depression with suicidal ideation or depression associated with chronic illness or anxiety such as, but not limited to, end-of-life anxiety, generalized anxiety disorder (GAD), social anxiety disorder (SAD), panic disorder, post-traumatic stress disorder (PTSD), obsessive-compulsive disorder (OCD), a phobia or performance anxiety. Nonlimiting examples of addictions which may be treated include alcohol use disorder (AUD), nicotine addiction, opioid use disorder, stimulant use disorder (i.e. cocaine or methamphetamine), cannabis use disorder, hallucinogen use disorder, sedative use disorder, hypnotic use disorder, or anxiolytic use disorder, gambling disorder, internet gaming disorder, food addiction and binge eating disorder, anorexia nervosa, compulsive sexual behavior disorder, compulsive buying disorder, and compulsive behavioral addictions. Nonlimiting examples of additional disorders or conditions which can be treated include attention deficit disorder, adult attention deficit disorder, autism spectrum disorder (ASD) with comorbid anxiety, autism spectrum disorder (ASD) with comorbid depression, anxiety and depression associated with neurodegenerative disorders, adjustment disorders, body dysmorphic disorder (BDD), memory disorders, personality disorders, and borderline personality disorder (BPD).

The following nonlimiting examples are provided to further illustrate the present invention.

EXAMPLE

Example 1: Preparation of Solid Psilocin Mucate Salt

Psilocin, 204.2 mg, (1.0 mmol) and galactaric acid (mucic acid), (1.0 mmol) were weighed into 8 ml vial and then 2.0 ml Methanol was added while being stirred using a magnetic bar. Precipitates formed right away with mucic acid. The precipitates were collected on a frit after diluting with about 4 mL of ethyl acetate. The collected products were washed successively with ethyl acetate and ether, and then dried under high vacuum.

Example 2: Collection of XRPD-Pattern

The XRPD patterns were collected using a Rigaku SmartLab SE diffractometer. The specimens were analyzed using Cu radiation produced using a 2.2 kW ceramic long fine-focus source. A flat multilayer mirror was used to focus the CuKα X-rays of the source to the specimen and onto the detector. The specimen was placed onto a zero-background sample holder, leveled with a glass slide, and analyzed in reflection geometry. The sample was rotated to optimize orientation statistics. A beam stop and an antiscatter knife edge were used to minimize the background generated by air. Soller slits for the incident and diffracted beams were used to minimize broadening from axial divergence. The diffraction pattern was collected using a scanning position-sensitive detector located 300 mm from the specimen. Data collection was carried out at room temperature between 2-40° 2θ at a scan rate of 5.0° per minute. Prior to the analysis, NIST SRM 675 was analyzed to verify the position of the (0 0 1) peaks over the specimen scan range.

Table 1 sets forth the measurement conditions

TABLE 1

| | |
|---|---|
| X-Ray generator | 40 kV, 40 mA |
| Incident primary | Standard |
| Goniometer | Standard Goniometer |
| Attachment | ASC-6 attachment (reflection geometry) |
| Filter | None |
| Selection slit | DB |
| Diffracted beam mono | None |
| Detector | None |
| Optics attribute | DB |
| Scan mode | 1D(scan) |
| Scan speed/Duration time | 5.00°/min |
| Step width | 0.01° |
| Scan axis | θ/2θ |
| Scan range | 2~40° |

TABLE 1-continued

| | |
|---|---|
| Incident slit box | 1/4 deg |
| Length-limiting slit | 10 mm |
| Receiving slit box #1 | None |
| Receiving slit box #2 | Open |

Table 2 sets forth the measured peak list.

TABLE 2

| No. | 2θ, ° | FWHM, ° | d, Å | Norm, I. |
|---|---|---|---|---|
| 1 | 4.80(19) | 1.91(16) | 18.4(7) | 3.41 |
| 2 | 7.836(3) | 0.141(3) | 11.274(4) | 11.73 |
| 3 | 8.7572(17) | 0.1762(13) | 10.0894(19) | 26.47 |
| 4 | 10.900(2) | 0.115(3) | 8.1100(16) | 6.31 |
| 5 | 13.024(4) | 0.240(3) | 6.7920(19) | 14.11 |
| 6 | 13.769(2) | 0.1751(18) | 6.4261(11) | 23.57 |
| 7 | 14.7147(14) | 0.1748(10) | 6.0152(6) | 100.00 |
| 8 | 15.200(12) | 0.111(9) | 5.824(4) | 2.10 |
| 9 | 15.7522(13) | 0.1726(11) | 5.6213(5) | 49.09 |
| 10 | 16.213(2) | 0.160(3) | 5.4624(7) | 8.90 |
| 11 | 16.425(2) | 0.162(8) | 5.3926(7) | 5.69 |
| 12 | 16.8039(14) | 0.1712(16) | 5.2718(4) | 21.53 |
| 13 | 17.592(4) | 0.219(9) | 5.0373(12) | 4.80 |
| 14 | 18.037(3) | 0.203(4) | 4.9141(8) | 11.75 |
| 15 | 18.503(4) | 0.259(3) | 4.7912(10) | 22.41 |
| 16 | 19.5746(18) | 0.1643(12) | 4.5314(4) | 45.08 |
| 17 | 20.066(7) | 0.13(2) | 4.4215(15) | 1.01 |
| 18 | 20.931(2) | 0.193(2) | 4.2408(5) | 36.48 |
| 19 | 21.497(3) | 0.207(3) | 4,1303(5) | 22.56 |
| 20 | 21.957(4) | 0.164(8) | 4.0448(7) | 5.23 |
| 21 | 22.361(3) | 0.192(3) | 3.9727(5) | 18.94 |
| 22 | 22.906(6) | 0.137(17) | 3.8793(11) | 5.43 |
| 23 | 23.203(5) | 0.240(5) | 3.8304(8) | 50.21 |
| 24 | 23.804(5) | 0.202(6) | 3.7350(8) | 27.36 |
| 25 | 25.05(2) | 0.173(17) | 3.551(3) | 6.34 |
| 26 | 25.744(3) | 0.173(6) | 3.4577(4) | 15.86 |
| 27 | 26.061(4) | 0.206(12) | 3.4164(5) | 12.82 |
| 28 | 26.782(8) | 0.487(16) | 3.3261(9) | 24.46 |
| 29 | 27.376(5) | 0.209(11) | 3.2552(6) | 7.95 |
| 30 | 28.613(18) | 0.230(13) | 3.1173(19) | 2.08 |
| 31 | 29.500(3) | 0.292(3) | 3.0255(3) | 17.84 |
| 32 | 30.251(5) | 0.270(11) | 2.9520(5) | 3.93 |
| 33 | 30.665(2) | 0.1956(18) | 2.9131(2) | 25.96 |
| 34 | 31.809(9) | 0.342(8) | 2.8110(7) | 5.65 |
| 35 | 32.369(7) | 0.191(14) | 2.7636(5) | 1.38 |
| 36 | 33.039(11) | 0.32(2) | 2.7090(9) | 6.32 |
| 37 | 33.247(6) | 0.130(17) | 2.6926(4) | 2.07 |
| 38 | 33.856(9) | 0.144(16) | 2.6455(7) | 1.25 |
| 39 | 34,018(10) | 0.11(2) | 2.6333(8) | 0.68 |
| 40 | 34.392(2) | 0.212(4) | 2.60550(17) | 10.86 |
| 41 | 34.792(3) | 0.282(6) | 2.5765(2) | 11.47 |
| 42 | 35.670(5) | 0.327(9) | 2.5150(4) | 4.52 |
| 43 | 36.596(4) | 0.326(4) | 2.4535(2) | 15.00 |
| 44 | 37.164(5) | 0.373(10) | 2.4173(3) | 8.54 |
| 45 | 37.506(4) | 0.112(5) | 2.3960(3) | 4.81 |
| 46 | 37.614(2) | 0.111(5) | 2.38942(12) | 9.19 |
| 47 | 38.367(8) | 0.331(17) | 2.3442(5) | 1.89 |
| 48 | 39.744(10) | 0.321(11) | 2.2661(5) | 3.46 |

Example 3: Stability Studies on Psilocin Mucate

Additional stability studies were performed on the solid psilocin form psilocin mucate (also known as psilocin mucic acid salt or conjugate or psilocin galactaric acid salt or conjugate) capsule.

Appearance was evaluated by viewing of the sample on a watchglass over a black and white background.

Assay conditions for Test/Method TM-022-0392 assessing stability and impurities were as follows:
Mobile phase: MPA: 945 mL water, 5 mL $H_3PO_4$, pH to 5.7 with
NaOH; MPB: Acetonitrile
Diluent: 80:20 Water: MeOH
Standard: 0.4 mg/mL Psilocin Mucic RS in Diluent
Sample: 0.4 mg/mL Psilocin Mucic API in Diluent
HPLC Conditions are depicted in Table 3.

TABLE 3

| Column | 4.6 mm × 250 mm, 5 µm column Zorbax SB-Phenyl or equivalent |
|---|---|
| Column temperature | 35° C. |
| Mobile phase | MPA—94.5: 0.5 Water: $H_3PO_4$ MPB—Acetonitrile |
| Flow rate | 1.0 mL/minute |
| Injection volume | 10 µL |
| Autosampler temperature | Ambient |
| Detector | 220 nm (200-400 nm for PDA) |
| Run Time | 45 minutes |
| Quantitation | Area percent |
| Approx Retention Time | Psilocin ~15 minutes |

| Gradient | Time (minutes) | % MPA | % MPB |
|---|---|---|---|
| | 0.0 | 95 | 5 |
| | 16 | 85 | 15 |
| | 20 | 85 | 15 |
| | 40 | 75 | 25 |
| | 40.1 | 95 | 5 |
| | 45* | 95 | 5 |

*Additional equilibration may be required
System suit: RSD NMT 2.0% (5 injections), Tailing NMT 2.0, Plate count NLT 10000

Calculations were against a bracketing external standard.
Identity of psilocin mucate was verified by ultraviolet (UV) assessment, wherein the UV spectrum of the main peak in the standard matched the UV spectrum of the main peak in the sample and by retention time wherein the retention time ratio was 0.98-1.02.
Results are depicted in the following Table 4.

TABLE 4

| Test/Method | Specification | Initial | 7 Months |
|---|---|---|---|
| Appearance | Product: White to light brown powder partially filling white opaque capsules Packaging: Labeled, amber glass bottle with white closure containing 15 partially filled white opaque capsules | Conforms Conforms | Conforms Conforms |
| Assay TM-22-0392 | 90.0-110.0% (% Label Claim) | 100.8% | 101.7% |
| Impurities TM-22-0392 | Report all impurities 0.05% Total Impurities—Report Results | RRT I.12/0.08% 0.08% | All <0.05% <0.05% |

Example 4: Phase One, Open-Label, Single-Treatment, Single-Dose, Single-Period, Pharmacokinetic Study of Hard Gelatin Capsules Containing the Solid Psilocin Form Psilocin Mucate For this study, psilocin mucate, a tryptamine derivative presenting as a white to light brown solid, crystalline powder was administered. The molecular weight of this compound 414.41 g/mol. With respect to equivalency, 4.05 mg of psilocin mucate is equivalent to 2 mg of psilocin. In humans, the mucic acid is enzymatically cleaved in the body during metabolism to produce psilocin, which serves as an agonist to various serotonin receptors including the 5-HT2A receptor, which underlies psilocin's hallucinogenic and therapeutic effects (Cao et al. Science (New York, N.Y.) 2022 375 (6579): 403-411; Lowe et al. Molecules 2021 26 (10), 2948). For this clinical study psilocin was provided as white/opaque hard gelatin capsules containing 4.05 mg of the psilocin mucate equivalent to 2 mg psilocin. A single capsule was administered orally, with water to 10 healthy subjects ages between 21 and 50 years, body-mass index 18.5 to 30.0 kg/m2 inclusive (minimum of 50 kg weight for males and 45 kg for females), non-smokers or quit smoking 24 hours prior to dosing. The aim of the study was to assess the bioavailability and pharmacokinetic parameters of the psilocin mucate by measurement of plasma concentrations of psilocin and calculations from those measurements.

Blood collection (8 mL) was performed in K3 EDTA blood tubes under sodium light at pre-dosing (−1.00) and at 0.25, 0.50, 0.75, 1.00, 1.50, 2.00, 3.00, 5.00, 8.00, 12.00, 16.00 and 24.00 hours after dosing.

The total number of blood collections in study period was 13.

In addition, a psychiatrist independent from the principal investigators of the study assessed the "mood" of each subject and gave each subject the mini mental state examination (MMSE) test to determine if the subject's score was lowered. The MMSE test is an 11-question measure that tests five areas of cognitive function: orientation, registration, attention and calculation, recall, and language. The MMSE scores, when a hallucinogenic substance is dosed, are expected to go down below 25 Results are depicted in the following Table 5.

TABLE 5

| SUBJECT NO. | MMSE | FEELING STATUS |
|---|---|---|
| 01 | 27 | More relaxed, want to drink sweet tea, better mood |
| 02 | 29 | Better mood, feels hyper sexual |
| 03 | 28 | Felt high mood, now he feels in good way,, he would love to tak eIMP daily |
| 04 | 29 | Less anxious, better mood, increase his appetite |
| 05 | 30 | Feel little beet happier, better energy |
| 06 | 28 | Feel calm, less thoughts, happier mood |
| 07 | 28 | Euphoric, better mood, it helps with life stress |
| 08 | 27 | Euphories, better mood, sleepy, feel time is slower |
| 09 | 30 | Sleepy, better thoughts, less worried in general |
| 10 | 30 | Did not feel change in mood but feeling cold extremities. |

Surprisingly, unlike results reported for psilocybin administration such as by Griffith et al. (Pharmaceutica Acta Helvetiae 2011 72 (3) 175-184.), 9 of the 10 subjects administered the psilocin mucate had no hallucinogenic effect but a strong suggestion of an anti-anxiolytic effect. These anti-anxiolytic effects at such a low dose, without the hallucinogenic effect was completely unexpected, particularly in a patient population undergoing blood draws often during this same time period.

What is claimed is:

1. A solid form of psilocin mucate, at least a portion of which is crystalline and is characterized by an X-ray powder diffraction (XRPD) pattern comprising peaks at about 14.71, 15.75, 19.57 and 23.20 2θ, ° using Cu Kα radiation.

2. The solid form of psilocin mucate of claim 1, wherein the crystalline portion is further characterized by XRPD pattern peaks at about 8.75, 20.93, 23.80 and 30.66 2θ, ° using Cu Kα radiation.

3. A pharmaceutical composition comprising the solid form of psilocin mucate of claim 1 and a pharmaceutically acceptable carrier.

4. An oral pharmaceutical composition comprising the solid form of psilocin mucate of claim 1 and an oral pharmaceutically acceptable carrier.

5. A method for treating a disease or condition in a subject treatable with psilocin or psilocybin, said method comprising administering to the subject the solid form of psilocin mucate of claim 1.

6. A method for treating a disease or condition in a subject treatable with psilocin or psilocybin, said method comprising administering to the subject the pharmaceutical composition of claim 3.

7. A method for treating a disease or condition in a subject treatable with psilocin or psilocybin, said method comprising orally administering to the subject the pharmaceutical composition of claim 4.

8. A solid form of psilocin, at least a portion of which is crystalline and is characterized by an X-ray powder diffraction (XRPD) pattern comprising peaks at 14.7147, 15.7522, 19.5746 and 23.203 2θ, ° using Cu Kα radiation.

9. The solid form of psilocin of claim 8, wherein the crystalline portion is further characterized by XRPD pattern peaks at 8.7572, 20.931, 23.804 and 30.665 2θ, ° using Cu Kα radiation.

10. A pharmaceutical composition comprising the solid form of psilocin of claim 8 and a pharmaceutically acceptable carrier.

11. An oral pharmaceutical composition comprising the solid form of psilocin of claim 8 and an oral pharmaceutically acceptable carrier.

12. A solid form of psilocin, at least a portion of which is crystalline and is characterized by an X-ray powder diffraction (XRPD) pattern using Cu Kα radiation depicted in FIG. 1.

* * * * *